(12) United States Patent
Aram et al.

(10) Patent No.: US 9,241,682 B2
(45) Date of Patent: Jan. 26, 2016

(54) APPARATUS AND METHOD FOR CALIBRATING AN X-RAY IMAGE OF A KNEE OF A PATIENT

(71) Applicant: DePuy Synthes Products, Inc., Raynham, MA (US)

(72) Inventors: Luke J. Aram, Warsaw, IN (US); Michael D. Goatbe, Cilo, MI (US); Carrie A. Leman, Chicago, IL (US); Ian M. Scott, Warsaw, IN (US); Graham R. Vincent, Cheshire (GB); Kevin M. Augustine de Souza, Ilkley (GB); Gwenael A. Guillard, Stockport (GB)

(73) Assignees: DEPUY SYNTHES PRODUCTS, INC, Raynham, MA (US); IMORPHICS, LTD. (GB)

( * ) Notice: Subject to any disclaimer, the term of this patent is extended or adjusted under 35 U.S.C. 154(b) by 333 days.

(21) Appl. No.: 13/797,131

(22) Filed: Mar. 12, 2013

(65) Prior Publication Data

US 2014/0270065 A1   Sep. 18, 2014

(51) Int. Cl.
*A61B 6/00* (2006.01)
*A61B 19/00* (2006.01)
*A61B 6/04* (2006.01)

(52) U.S. Cl.
CPC ............. *A61B 6/583* (2013.01); *A61B 6/0492* (2013.01); *A61B 6/505* (2013.01); *A61B 2019/5289* (2013.01); *A61B 2019/5466* (2013.01)

(58) Field of Classification Search
CPC ................... A61B 19/54; A61B 6/583; A61B 2019/5466; A61B 5/4585; A61B 5/70; A61B 6/0492
See application file for complete search history.

(56) References Cited

U.S. PATENT DOCUMENTS

| 5,224,147 A | 6/1993 | Collin et al. | |
| 5,681,326 A * | 10/1997 | Lax | 378/163 |
| 5,835,563 A | 11/1998 | Navab et al. | |
| 5,970,119 A | 10/1999 | Hofmann | |
| 7,922,391 B2 | 4/2011 | Essenreiter et al. | |
| 2002/0041655 A1 | 4/2002 | Mitschke | |
| 2004/0093673 A1* | 5/2004 | Marshall | 5/650 |
| 2007/0269016 A1 | 11/2007 | Mackey | |
| 2009/0018437 A1* | 1/2009 | Cooke | 600/427 |
| 2010/0135467 A1 | 6/2010 | King et al. | |

FOREIGN PATENT DOCUMENTS

| DE | 102005006775 A1 | 8/2006 |
| EP | 2543320 A1 | 1/2013 |
| WO | 2004023103 A2 | 3/2004 |
| WO | 2006087263 | 8/2006 |

OTHER PUBLICATIONS

PCT International Search Report for International Application No. PCT/US2014/017166, Feb. 10, 2014, 4 pages.

* cited by examiner

*Primary Examiner* — Glen Kao
(74) *Attorney, Agent, or Firm* — Barnes & Thornburg, LLP

(57) ABSTRACT

An x-ray calibration apparatus includes a radiolucent knee alignment jig configured to receive a knee of a patient and a radiolucent cushion configured to hold a patient's knee at a fixed angle of flexion. The x-ray calibration apparatus also includes a number of radio-opaque fiducial markers positioned within the radiolucent knee alignment jig.

7 Claims, 19 Drawing Sheets

APPARATUS AND METHOD FOR CALIBRATING AN X-RAY IMAGE OF A KNEE OF A PATIENT

TECHNICAL FIELD

The present disclosure relates generally to customized patient-specific orthopaedic surgical instruments, and in particular to an x-ray calibration apparatus and method.

BACKGROUND

Joint arthroplasty is a well-known surgical procedure by which a diseased and/or damaged natural joint is replaced by a prosthetic joint. A typical knee prosthesis includes a tibial tray, a femoral component, a polymer insert or bearing positioned between the tibial tray and the femoral component, and, in some cases, a polymer patella button. To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

SUMMARY

According to one aspect, an x-ray calibration apparatus includes a radiolucent knee alignment jig configured to receive a knee of a patient. The radiolucent knee alignment jig includes a bottom plate, a lateral sidewall secured to and extending upwardly from a lateral side of the bottom plate, and a medial sidewall secured to and extending upwardly from a medial side of the bottom plate. The x-ray calibration apparatus also includes a first plurality of radio-opaque fiducial markers positioned within the lateral sidewall and a second plurality of radio-opaque fiducial markers positioned within the medial sidewall. The second plurality of radio-opaque fiducial markers are positioned such that when viewed in an x-ray image taken perpendicularly to the bottom plate, each of the second plurality of radio-opaque fiducial markers are distinct from the first plurality of radio-opaque fiducial markers, and when viewed in an x-ray image taken perpendicularly to the lateral sidewall, each of the second plurality of radio-opaque fiducial markers are distinct from the first plurality of radio-opaque fiducial markers.

In an embodiment, the medial sidewall is shorter than the lateral sidewall.

The x-ray calibration apparatus may also include a radiolucent cushion configured to hold a patient's knee at a fixed angle of flexion, the cushion being secured to an upper surface of the bottom plate and positioned between the lateral sidewall and the medial sidewall.

In an embodiment, the first plurality of radio-opaque fiducial markers includes an upper lateral plurality of radio-opaque fiducial markers, positioned within the lateral sidewall such that when viewed in an x-ray image taken perpendicularly to the lateral sidewall, each of the upper lateral plurality of radio-opaque fiducial markers appears above an upper ridge of the radiolucent cushion. The first plurality of radio-opaque fiducial markers also includes a lower lateral plurality of radio-opaque fiducial markers, positioned within the lateral sidewall such that when viewed in an x-ray image taken perpendicularly to the lateral sidewall, each of the lower lateral plurality of radio-opaque fiducial markers appears below the upper ridge of the radiolucent cushion.

The upper lateral plurality of radio-opaque fiducial markers may consist of three radio-opaque fiducial markers, the lower lateral plurality of radio-opaque fiducial markers may consist of three radio-opaque fiducial markers, and the second plurality of radio-opaque fiducial markers may consist of four radio-opaque fiducial markers.

According to another aspect, an x-ray calibration apparatus includes a radiolucent knee alignment jig configured to receive a knee of a patient, the knee alignment jig. The radiolucent knee alignment jig includes a bottom plate, a lateral sidewall secured to and extending upwardly from a lateral side of the bottom plate, and a medial sidewall secured to and extending upwardly from a medial side of the bottom plate. The x-ray calibration apparatus also includes a radiolucent cushion configured to hold a patient's knee at a fixed angle of flexion. The cushion is secured to an upper surface of the bottom plate and positioned between the lateral sidewall and the medial sidewall. The x-ray calibration apparatus also includes a first plurality of radio-opaque fiducial markers, positioned such that when viewed in an x-ray image taken perpendicularly to the lateral sidewall, each of the first plurality of radio-opaque fiducial markers appears above an upper ridge of the radiolucent cushion; a second plurality of radio-opaque fiducial markers, positioned such that when viewed in an x-ray image taken perpendicularly to the lateral sidewall, each of the second plurality of radio-opaque fiducial markers appears below the upper ridge of the radiolucent cushion; and a third plurality of radio-opaque fiducial markers positioned such that when viewed in an x-ray image taken perpendicularly to the bottom plate, each of the third plurality of radio-opaque fiducial markers is distinct from each of the first and second plurality of radio-opaque fiducial markers, and when viewed in an x-ray image taken perpendicularly to the lateral sidewall, each of the third plurality of radio-opaque fiducial markers is distinct from each of the first and second plurality of radio-opaque fiducial markers.

The radiolucent cushion may be marked with intersecting perpendicular lines configured to be aligned with cross-hairs emitted by an x-ray source positioned to create an x-ray image taken perpendicularly to the bottom plate. The lateral sidewall also may be marked with intersecting perpendicular lines configured to be aligned with cross-hairs emitted by an x-ray source positioned to create an x-ray image taken perpendicularly to the lateral sidewall.

In an embodiment, the first plurality of radio-opaque fiducial markers are positioned within the lateral sidewall, the second plurality of radio-opaque fiducial markers are positioned within the lateral sidewall, and the third plurality of radio-opaque fiducial markers are positioned within the medial sidewall.

The first plurality of radio-opaque fiducial markers may consist of three radio-opaque fiducial markers, the second plurality of radio-opaque fiducial markers may consist of three radio-opaque fiducial markers, and the third plurality of radio-opaque fiducial markers may consist of four radio-opaque fiducial markers.

According to another aspect, a method of generating an image for use in the fabrication of a customized patient-specific orthopaedic knee instrument includes positioning a patient's knee on an x-ray calibration apparatus having a plurality of radio-opaque fiducial markers positioned at fixed distances such that each of the plurality of radio-opaque fiducial markers are distinct from one another when viewed in x-ray images taken in a direction anterior to the patient's knee, and in a direction lateral to the patient's knee. A first x-ray image is taken in a direction anterior to the patient's knee such that representations of at least some of the plurality of radio-opaque fiducial markers are visible in the first x-ray image. A second x-ray image is taken in a direction lateral to the patient's knee such that representations of at least some of the plurality of radio-opaque fiducial markers are visible in the second x-ray image. The first and second x-ray images are registered onto one another using the representations of the plurality of radio-opaque fiducial markers visible in the first and second x-ray images.

Registering the first and second x-ray images onto one another may include aligning the first and second x-ray images using the representations of the plurality of radio-opaque fiducial markers visible in the first and second x-ray images.

The method may also include calculating an x-ray scaling factor by measuring the distances between two or more of the representations of the plurality of radio-opaque fiducial markers visible in one or both of the first and second x-ray images, and comparing the distances between the two or more of the representations of the plurality of radio-opaque fiducial markers visible in one or both of the first and second x-ray images to the distances between the corresponding fiducial markers positioned in the x-ray calibration apparatus.

The method may also include calculating a beam angle by measuring the distances between two or more sets of representations of the plurality of radio-opaque fiducial markers visible in one or both of the first and second x-ray images, and comparing the distances between the two or more of the representations of the plurality of radio-opaque fiducial markers visible in one or both of the first and second x-ray images to the distances between the corresponding fiducial markers positioned in the x-ray calibration apparatus.

In an embodiment, the method may include calculating an x-ray scaling factor by measuring the distance between a first representation of a first of the plurality of radio-opaque fiducial markers visible in the first x-ray image and a second representation of a second of the plurality of radio-opaque fiducial markers visible in the first x-ray image, and comparing the distance between the first and second representations to the distance between the first fiducial marker positioned in the x-ray calibration apparatus and the second fiducial marker positioned in the x-ray calibration apparatus.

In an embodiment, the method may include calculating an x-ray scaling factor by measuring the distance between a first representation of a first of the plurality of radio-opaque fiducial markers visible in the second x-ray image and a second representation of a second of the plurality of radio-opaque fiducial markers visible in the second x-ray image, and comparing the distance between the first and second representations to the distance between the first fiducial marker positioned in the x-ray calibration apparatus and the second fiducial marker positioned in the x-ray calibration apparatus.

In an embodiment, the method may include calculating a beam angle by measuring the distances between two or more sets of representations of the plurality of radio-opaque fiducial markers visible in the first x-ray image, and comparing the distances between the two or more of the representations of the plurality of radio-opaque fiducial markers visible in the first x-ray image to the distances between the corresponding fiducial markers positioned in the x-ray calibration apparatus.

In an embodiment, the method may include calculating a beam angle by measuring the distances between two or more sets of representations of the plurality of radio-opaque fiducial markers visible in the second x-ray image, and (ii) comparing the distances between the two or more of the representations of the plurality of radio-opaque fiducial markers visible in the second x-ray image to the distances between the corresponding fiducial markers positioned in the x-ray calibration apparatus.

The method may also include generating a design of the customized, patient-specific orthopaedic knee instrument based on the registered first and second x-ray images.

BRIEF DESCRIPTION OF THE DRAWINGS

The detailed description particularly refers to the following figures, in which.

DETAILED DESCRIPTION OF THE DRAWINGS

Figure 1:
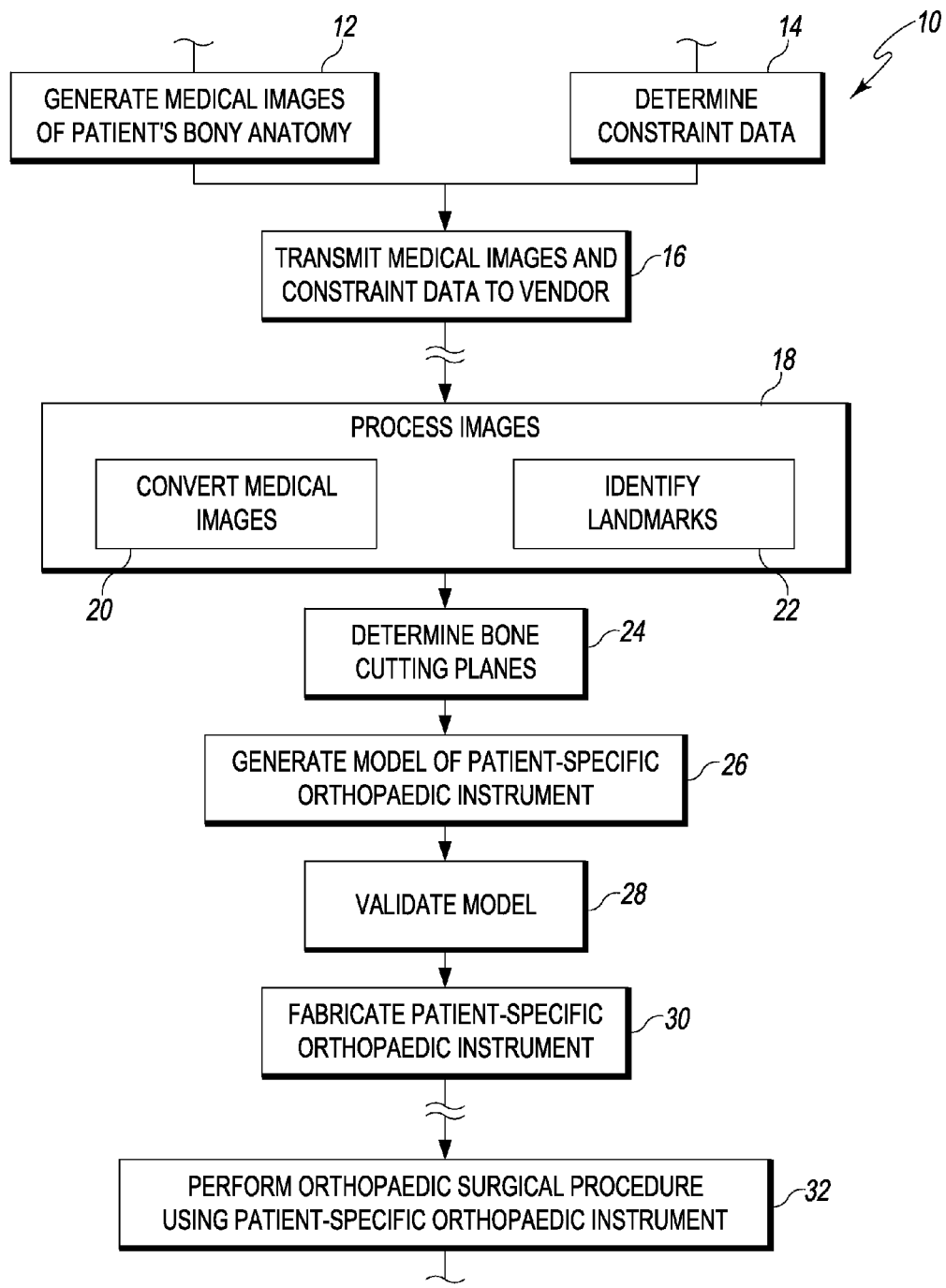
FIG. 1 is a simplified flow diagram of an algorithm for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to the orthopaedic implants and instruments described herein, along with a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses. Examples of "customized patient-specific orthopaedic surgical instruments" include customized patient-specific drill/pin guides, customized patient-specific tibial cutting blocks, and customized patient-specific femoral cutting blocks.

In some embodiments, the customized patient-specific orthopaedic surgical instrument may be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intra-operative decision-making with respect to the placement of the orthopaedic surgical instrument are reduced. For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument on the bone or bones of the patient in the unique location. When so coupled, the cutting plane, drilling/pinning holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling/pin guide, a milling guide, or other type of orthopaedic surgical instrument configured to be coupled to a bone of a patient.

As shown in FIG. 1, the algorithm 10 includes process steps 12 and 14, in which an orthopaedic surgeon performs pre-operative planning of the orthopaedic surgical procedure to be performed on a patient. The process steps 12 and 14 may be performed in any order or contemporaneously with each other. In process step 12, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as any number of computed tomography (CT) images, magnetic resonance imaging (MRI) images, or other three-dimensional medical images. Additionally or alternatively, as discussed in more detail below in regard to process step 18, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's knee joint.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for a metal-on-metal interface, amount of inclination for implantation, the thickness of the bone to resect, size range of the orthopaedic implant, and/or the like. In some embodiments, the orthopaedic surgeon's preferences are saved as a surgeon's profile, which may used as a default constraint values for further surgical plans.

In process step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer process the medical images to facilitate the determination of the bone cutting planes, implant sizing, and fabrication of the customized patient-specific orthopaedic surgical instrument as discussed in more detail below. For example, in process step 20 the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershead, or shape-matching algorithm may be used to convert or reconstruct images to a format acceptable in a computer aided design application or other image processing application. Further, in some embodiments, an algorithm may be used to account for tissue such as cartilage not discernable in the generated medical images. In such embodiments, any three-dimensional model of the patient-specific instrument (see, e.g., process step 26 below) may be modified according to such algorithm to increase the fit and function of the instrument.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the cutting planes of the patient's bone are determined. The planned cutting planes are determined based on the type, size, and position of the orthopaedic prosthesis to be used during the orthopaedic surgical procedure, on the process images such as specific landmarks identified in the images, and on the constraint data supplied by the orthopaedic surgeon in process steps 14 and 16. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bony anatomy of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the selected orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's rotation with respect to bony landmarks such as the femoral epicondyle, posterior condyles, sulcus groove (Whiteside's line), and the mechanical axis as defined by the hip, knee, and/or ankle centers.

The planned cutting planes for the patient's bone(s) may then be determined based on the determined size, location, and orientation of the orthopaedic prosthesis. In addition, other aspects of the patient's bony anatomy, as determined in process step 22, may be used to determine or adjust the planned cutting planes. For example, the determined mechanical axis, landmarks, and/or other determined aspects of the relevant bones of the patient may be used to determine the planned cutting planes.

In process step 26, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the customized patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling/pinning guide, a milling guide, and/or any other type of orthopaedic surgical tool or instrument.

The particular shape of the customized patient-specific orthopaedic surgical instrument is determined based on the planned location of the orthopaedic surgical instrument relative to the patient's bony anatomy. The location of the customized patient-specific orthopaedic surgical instrument with respect to the patient's bony anatomy is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 24. For example, in embodiments wherein the customized patient-specific orthopaedic surgical instrument is embodied as a drilling/pinning guide (or hereinafter, simply a "pin guide") for use in conjunction with a patient-universal cutting block, the location of the orthopaedic surgical instrument is selected such that the cutting guide of the patient-universal cutting block, when installed on guide pins placed in the bone by use of the customized patient-specific pin guide, matches one or more of the planned cutting planes determined in process step 24. Additionally, the planned location of the orthopaedic surgical instrument may be based on the identified landmarks of the patient's bone identified in process step 22.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to one or more of the bone cutting plane(s) as discussed above.

One illustrative embodiment of a method 40 for generating a model, such as a computer model, of a patient-specific orthopaedic instrument is illustrated in FIGS. 2 through 9. The method 40 begins with a step 42 in which a cartilage thickness value is determined. The cartilage thickness value is indicative of the average thickness of the cartilage of the patient's bone. As such, in one embodiment, the cartilage thickness value is equal to the average thickness of cartilage for an individual having similar characteristics as the patient. For example, the cartilage thickness value may be equal to the average thickness value of individuals of the same gender as the patient, the same age as the patient, having the same activity level of the patient, and/or the like. In other embodiments, the cartilage thickness value is determined based on one or more medical images of the patient's bone, such as those images transmitted in process step 16.

In step 44, a reference contour of the patient's relevant bone is determined. The reference contour is based on the surface contour of a three-dimensional model of the patient's relevant bone, such as the three-dimensional model generated in step 20. Initially the reference contour is identical to a region (i.e. the region of interest such as the distal end of the patient's femur or the proximal end of the patient's tibia) of the patient's bone. That is, in some embodiments, the reference contour is juxtaposed on the surface contour of the region of the patient's bone.

Subsequently, in step 46, the reference contour is scaled to compensate for the cartilage thickness value determined in step 42. To do so, in one embodiment, the scale of the reference contour is increased based on the cartilage thickness value. For example, the scale of the reference contour may be increased by an amount equal to or determined from the cartilage thickness value. However, in other embodiments, the reference contour may be scaled using other techniques designed to scale the reference contour to a size at which the reference contour is compensated for the thickness of the cartilage on the patient's bone.

Figure 3:
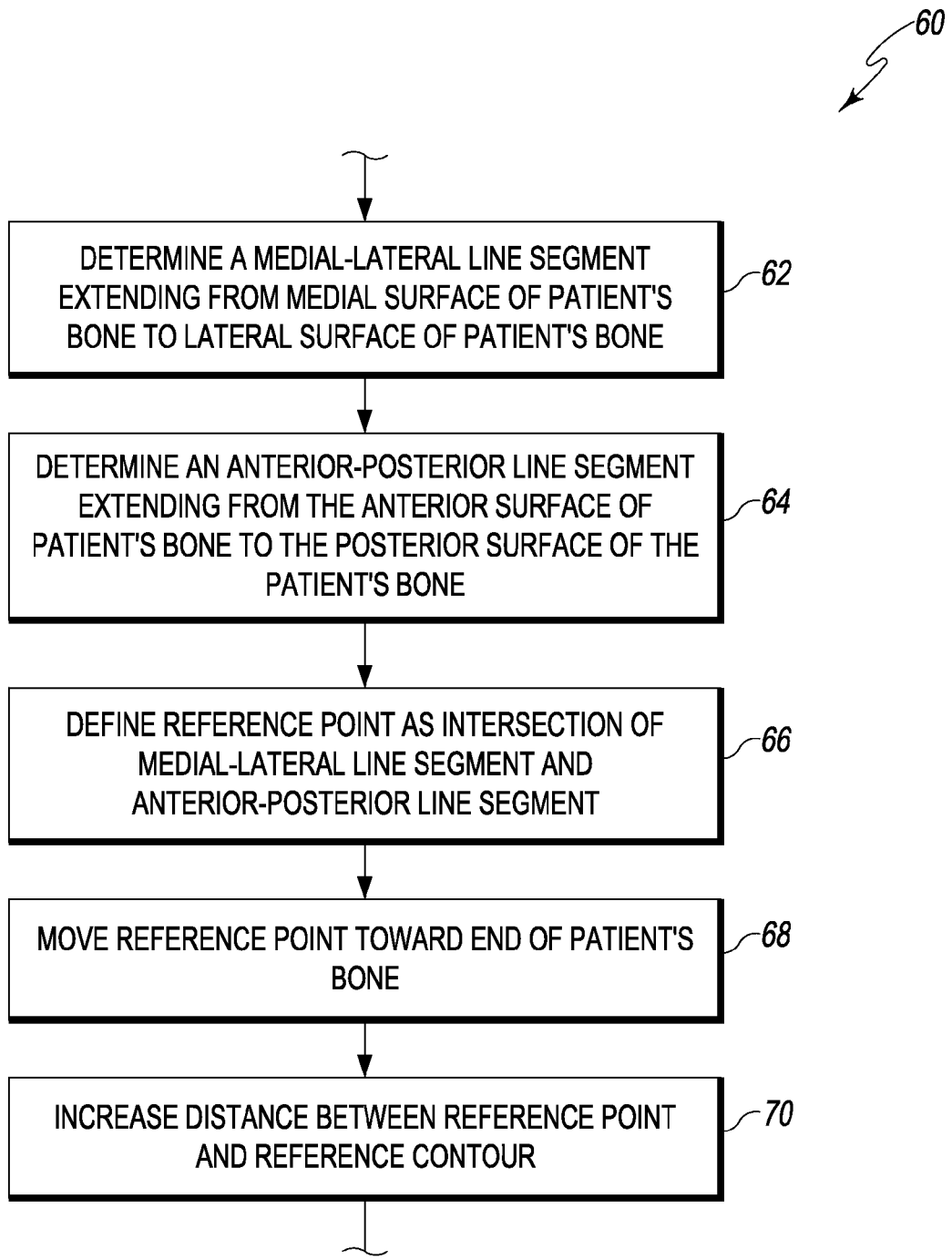
FIG. 3 is a simplified flow diagram of a method for scaling a reference contour.

For example, in one particular embodiment, the reference contour is scaled by increasing the distance between a fixed reference point and a point lying on, and defining in part, the reference contour. To do so, in one embodiment, a method 60 for scaling a reference contour as illustrated in FIG. 3 may be used. The method 60 begins with step 62 in which a medial/lateral line segment is established on the three-dimensional model of the patient's relevant bone. The medial/lateral line segment is defined or otherwise selected so as to extend from a point lying on the medial surface of the patient's bone to a point lying on lateral surface of the patient's bone. The medial surface point and the lateral surface point may be selected so as to define the substantially maximum local medial/lateral width of the patient's bone in some embodiments.

In step 64, an anterior/posterior line segment is established on the three-dimensional model of the patient's relevant bone. The anterior/posterior line segment is defined or otherwise selected so as to extend from a point lying on the anterior surface of the patient's bone to a point lying on posterior surface of the patient's bone. The anterior surface point and the posterior surface point may be selected so as to define the substantially maximum local anterior/posterior width of the patient's bone in some embodiments.

The reference point from which the reference contour will be scaled is defined in step 66 as the intersection point of the medial/lateral line segment and anterior/posterior line segment. As such, it should be appreciated that the medial surface point, the lateral surface point, the anterior surface point, and the posterior surface point lie on the same plane. After the reference point is initially established in step 66, the reference point is moved or otherwise translated toward an end of the patient's bone. For example, in embodiments wherein the patient's bone is embodied as a femur, the reference point is moved inferiorly toward the distal end of the patient's femur. Conversely, in embodiments when the patient's bone is embodied as a tibia, the reference point is moved superiorly toward the proximal end of the patient's tibia. In one embodiment, the reference point is moved a distance equal to about half the length of the anterior/posterior line segment as determined in step 64. However, in other embodiments, the reference point may be moved other distances sufficient to compensate the reference contour for thickness of the cartilage present on the patient's bone.

Once the location of the reference point has been determined in step 68, the distance between the reference point and each point lying on, and defining in part, the reference contour is increased in step 70. To do so, in one particular embodiment, each point of the reference contour is moved a distance away from the reference point based on a percentage value of the original distance defined between the reference point and the particular point on the reference contour. For example, in one embodiment, each point lying on, and defining in part, the reference contour is moved away from the reference point in by a distance equal to a percentage value of the original distance between the reference point and the particular point. In one embodiment, the percentage value is in the range of about five percent to about thirty percent. In one particular embodiment, the percentage value is about ten percent.

Figure 4:
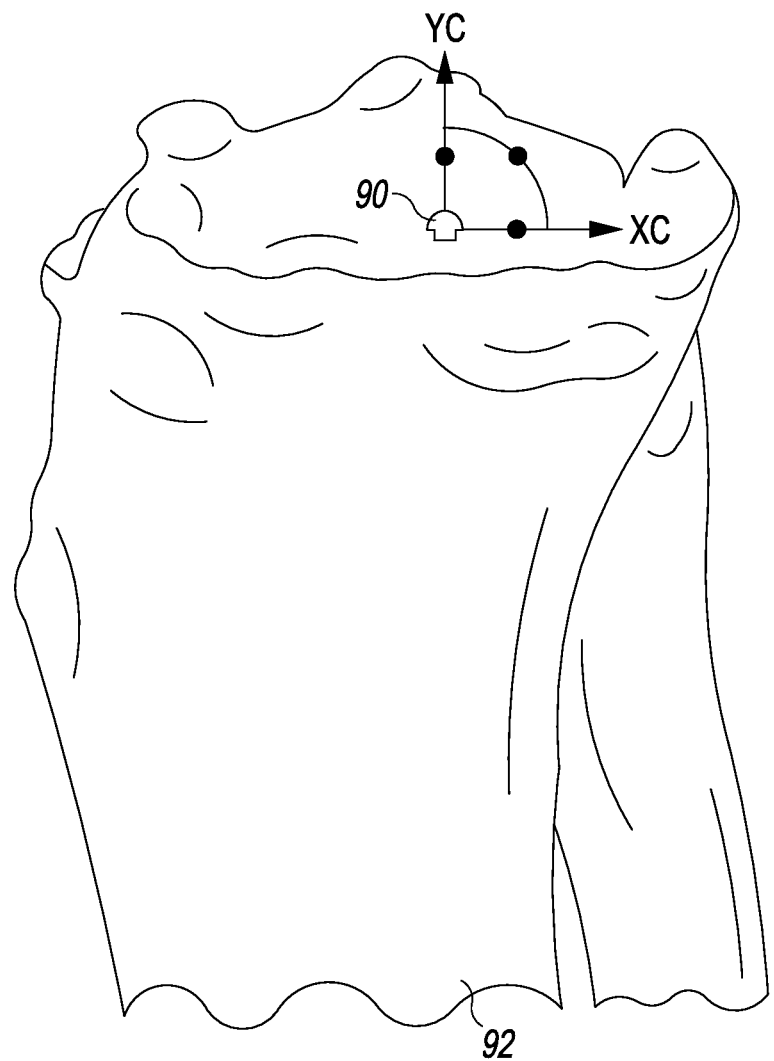
FIGS. 4-6 are three-dimensional model's of a patient's tibia.
Figure 5:
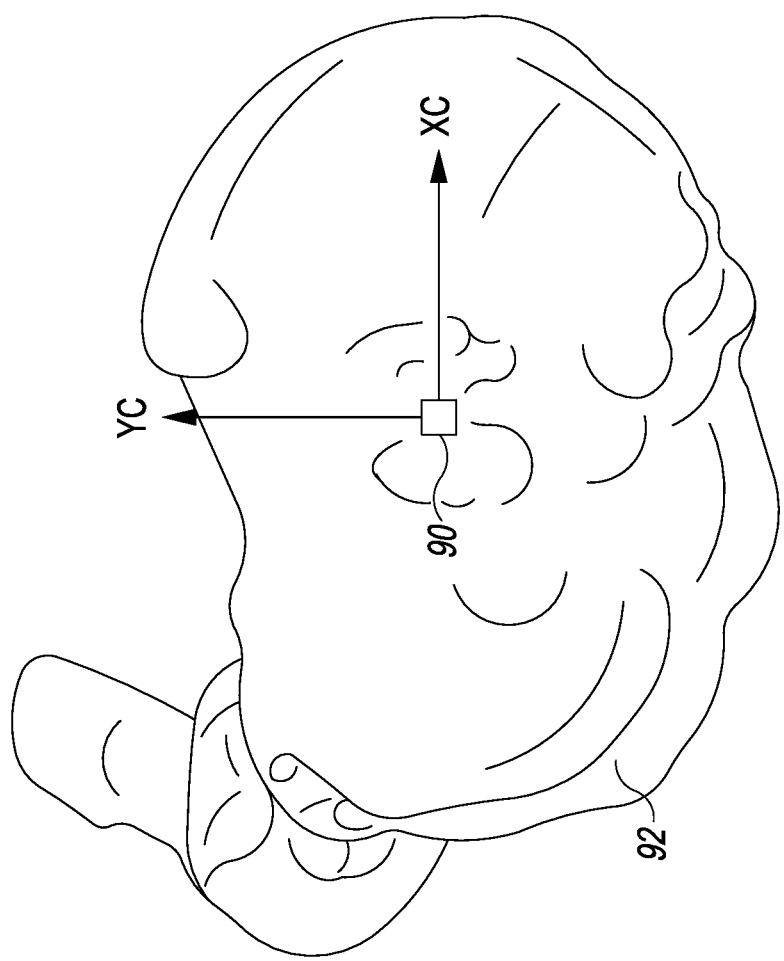
Figure 6:
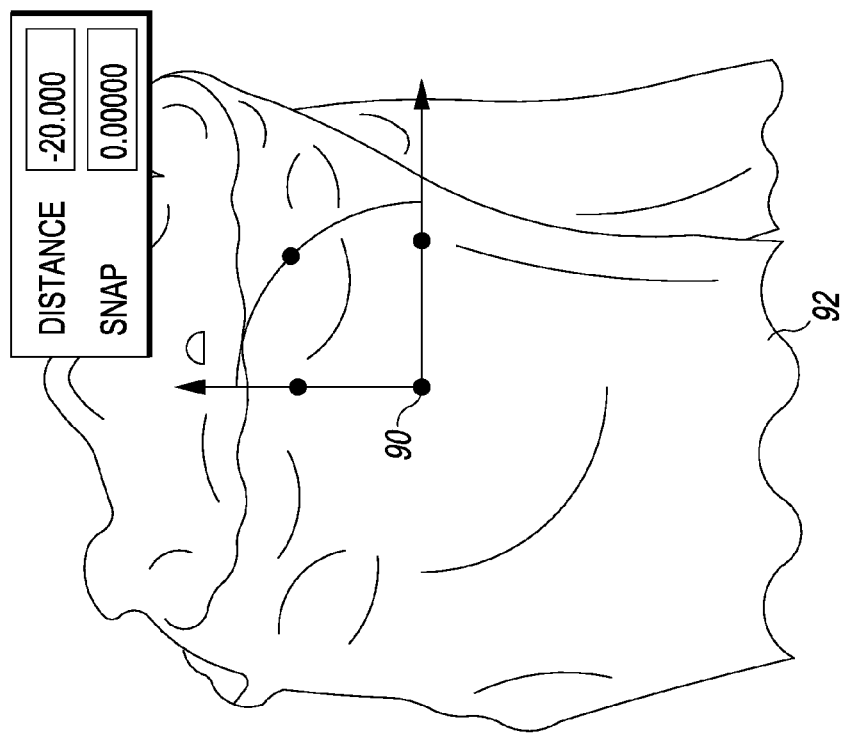

Referring now to FIGS. 4-9, in another embodiment, the reference contour is scaled by manually selecting a local "high" point on the surface contour of the three-dimensional image of the patient's bone. For example, in embodiments wherein the relevant patient's bone is embodied as a tibia as illustrated in FIGS. 4-6, the reference point 90 is initially located on the tibial plateau high point of the tibial model 92. Either side of the tibial plateau may be used. Once the reference point 90 is initially established on the tibial plateau high point, the reference point 90 is translated to the approximate center of the plateau as illustrated in FIG. 5 such that the Z-axis defining the reference point is parallel to the mechanical axis of the tibial model 92. Subsequently, as illustrated in FIG. 6, the reference point is moved in the distal direction by a predetermined amount. In one particular embodiment, the reference point is moved is the distal direction by about 20 millimeters, but other distances may be used in other embodiments. For example, the distance over which the reference point is moved may be based on the cartilage thickness value in some embodiments.

Figure 7:
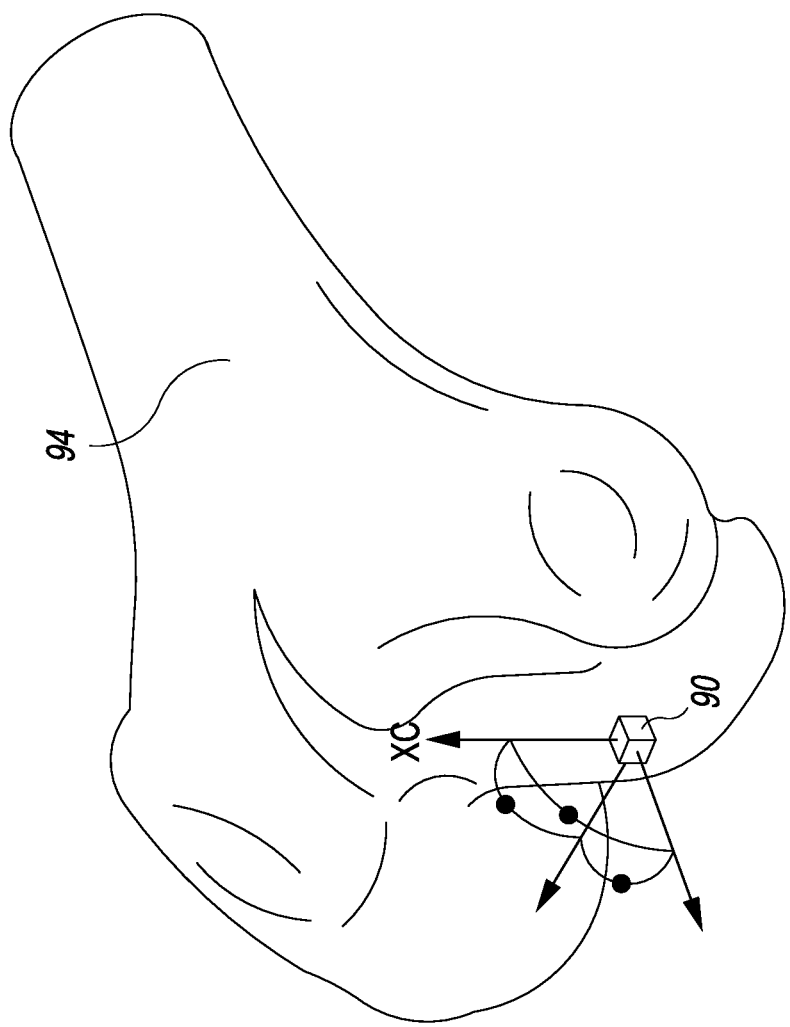
FIG. 7-9 are three-dimensional models of a patient's femur.
Figure 8:
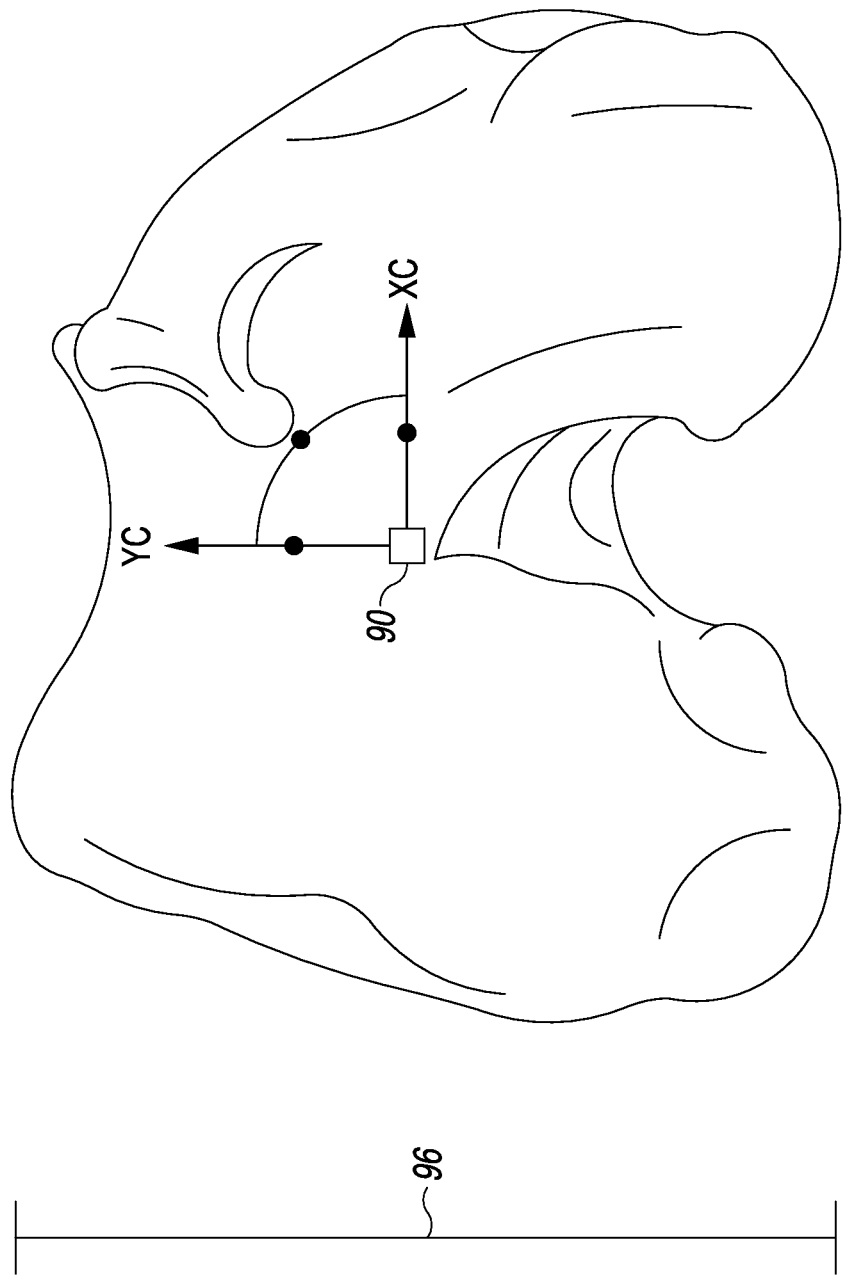
Figure 9:
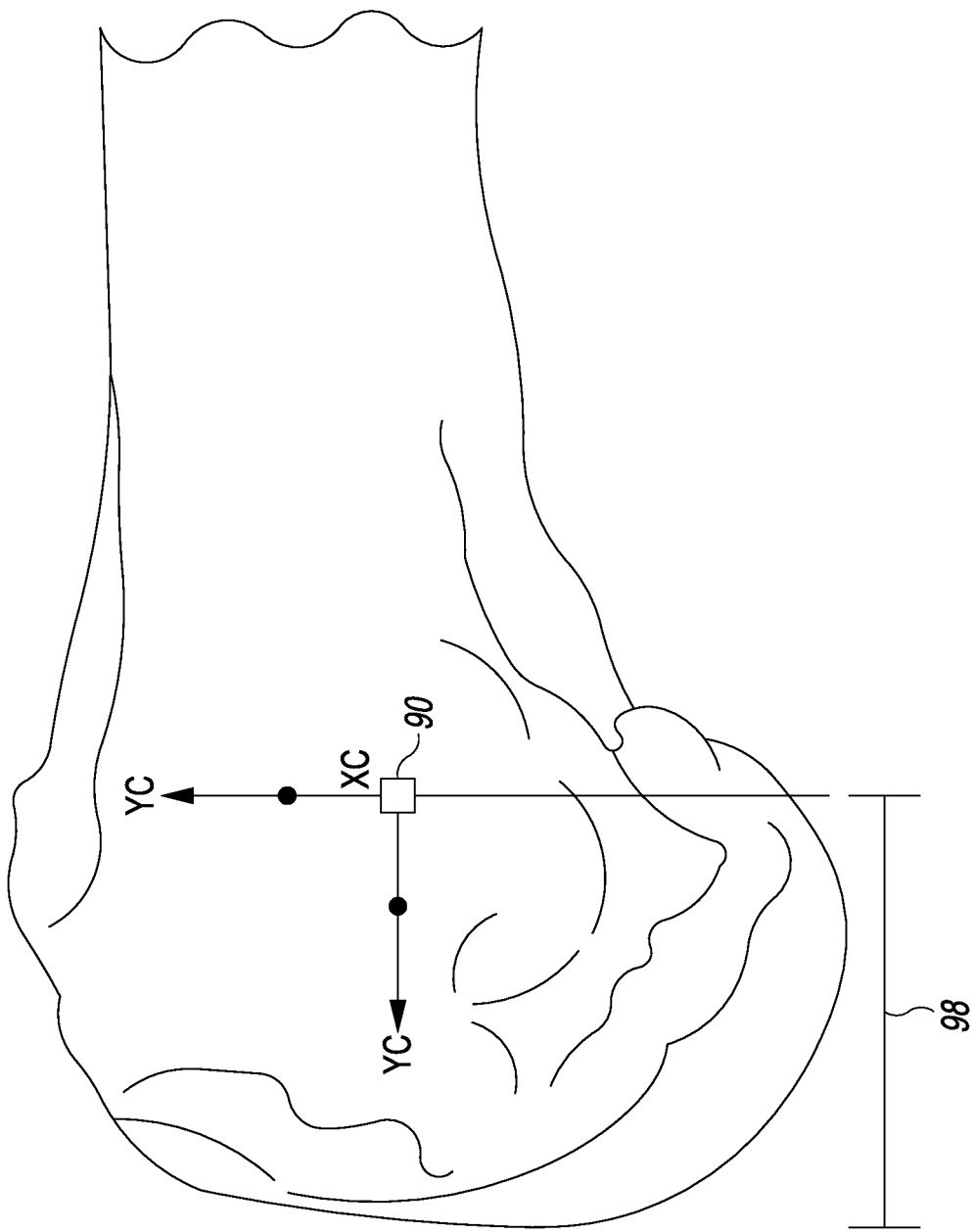

Conversely, in embodiments wherein the relevant patient's bone is embodied as a femur as illustrated in FIGS. 7-9, the reference point 90 is initially located on the most distal point of the distal end of the femoral model 94. Either condyle of the femoral model 94 may be used in various embodiments. Once the reference point 90 is initially established on the most distal point, the reference point 90 is translated to the approximate center of the distal end of the femoral model 94 as illustrated in FIG. 8 such that the Z-axis defining the reference point 90 is parallel to the mechanical axis of the femoral model 92. The anterior-posterior width 96 of the distal end of the femoral model 94 is also determined. Subsequently, as illustrated in FIG. 9, the reference point is moved or otherwise translated in the proximal or superior direction by a distance 98. In one particular embodiment, the reference point is moved in the distal or superior direction by a distance 98 equal to about half the distance 96. As such, it should be appreciated that one of a number of different techniques may be used to define the location of the reference point based on, for example, the type of bone.

Figure 2:
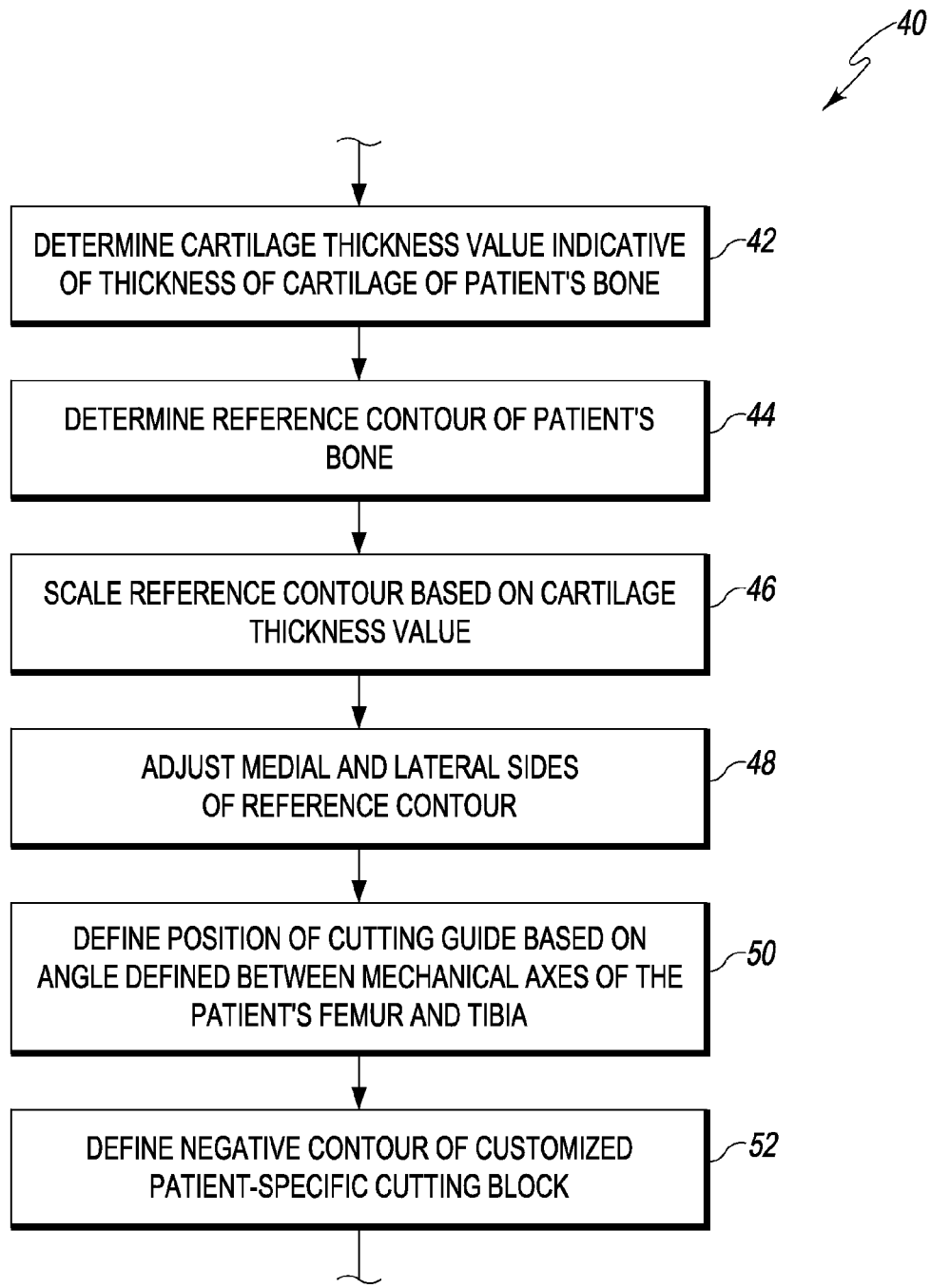
FIG. 2 is a simplified flow diagram of a method for generating a model of a patient-specific orthopaedic instrument.

Referring now back to FIG. 2, once the reference contour has been scaled in step 46, the medial/lateral sides of the reference contour are adjusted in step 48. To do so, in one embodiment, the distance between the reference point and each point lying on, and defining in part, the medial side and lateral side of the reference contour is decreased. For example, in some embodiments, the distance between the reference point and the points on the medial and lateral sides of the scaled reference contour are decreased to the original distance between such points. As such, it should be appreciated that the reference contour is offset or otherwise enlarged with respect to the anterior side of the patient's bone and substantially matches or is otherwise not scaled with respect to the medial and lateral sides of the patient's bone.

The reference contour may also be adjusted in step 48 for areas of the patient's bone having a reduced thickness of cartilage. Such areas of reduced cartilage thickness may be determined based on the existence of bone-on-bone contact as identified in a medical image, simulation, or the like. Additionally, information indicative of such areas may be provided by the orthopaedic surgeon based on his/her expertise. If one or more areas of reduced cartilage thickness are identified, the reference contour corresponding to such areas of the patient's bone is reduced (i.e., scaled back or down).

Additionally, in some embodiments, one or more osteophytes on the patient's bone may be identified; and the reference contour may be compensated for such presence of the osteophytes. By compensating for such osteophytes, the reference contour more closely matches the surface contour of the patient's bone. Further, in some embodiments, a distal end (in embodiments wherein the patient's bone is embodied as a tibia) or a proximal end (in embodiments wherein the patient's bone is embodied as a femur) of the reference contour may be adjusted to increase the conformity of the reference contour to the surface contour of the bone. For example, in embodiments wherein the patient's bone is a femur, the superior end of the scaled reference contour may be reduced or otherwise moved closer to the surface contour of the patient's femur in the region located superiorly to a cartilage demarcation line defined on the patient's femur. Conversely, in embodiments wherein the patient's bone is embodied as a tibia, an inferior end of the scaled reference contour may be reduced or otherwise moved closer to the surface contour of the patient's tibia in the region located inferiorly to a cartilage demarcation line of the patient's tibia. As such, it should be appreciated that the scaled reference contour is initially enlarged to compensate for the thickness of the patient's cartilage on the patient's bone. Portions of the scaled reference contour are then reduced or otherwise moved back to original positions and/or toward the reference point in those areas where cartilage is lacking, reduced, or otherwise not present.

Once the reference contour has been scaled and adjusted in steps 46 and 48, the position of the cutting guide is defined in step 50. In particular, the position of the cutting guide is defined based on an angle defined between a mechanical axis of the patient's femur and a mechanical axis of the patient's tibia. The angle may be determined by establishing a line segment or ray originating from the proximal end of the patient's femur to the distal end of the patient's femur and defining a second line segment or ray extending from the patient's ankle through the proximal end of the patient's tibia. The angle defined by these two line segments/rays is equal to the angle defined between the mechanical axis of the patient's femur and tibia. The position of the bone cutting guide is then determined based on the angle between the mechanical axes of the patient's femur and tibia. It should be appreciated that, as will be discussed below in more detail, the position of the cutting guide defines the position and orientation of the cutting plane of a patient-universal cutting block when it is installed on guide pins placed in the bone by use of a customized patient-specific pin guide. Subsequently, in step 52, a negative contour of the customized patient-specific pin guide is defined based on the scaled and adjusted reference contour and the angle defined between the mechanical axis of the femur and tibia.

Referring back to FIG. 1, after the model of the customized patient-specific orthopaedic surgical instrument has been generated in process step 26, the model is validated in process step 28. The model may be validated by, for example, analyzing the rendered model while coupled to the three-dimensional model of the patient's anatomy to verify the correlation of cutting guides and planes, drilling guides and planned drill points, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

After the model has been validated in process step 28, the customized patient-specific orthopaedic surgical instrument is fabricated in process step 30. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. The fabricated customized patient-specific orthopaedic instrument is subsequently shipped or otherwise provided to the orthopaedic surgeon. The surgeon performs the orthopaedic surgical procedure in process step 32 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Figure 10:
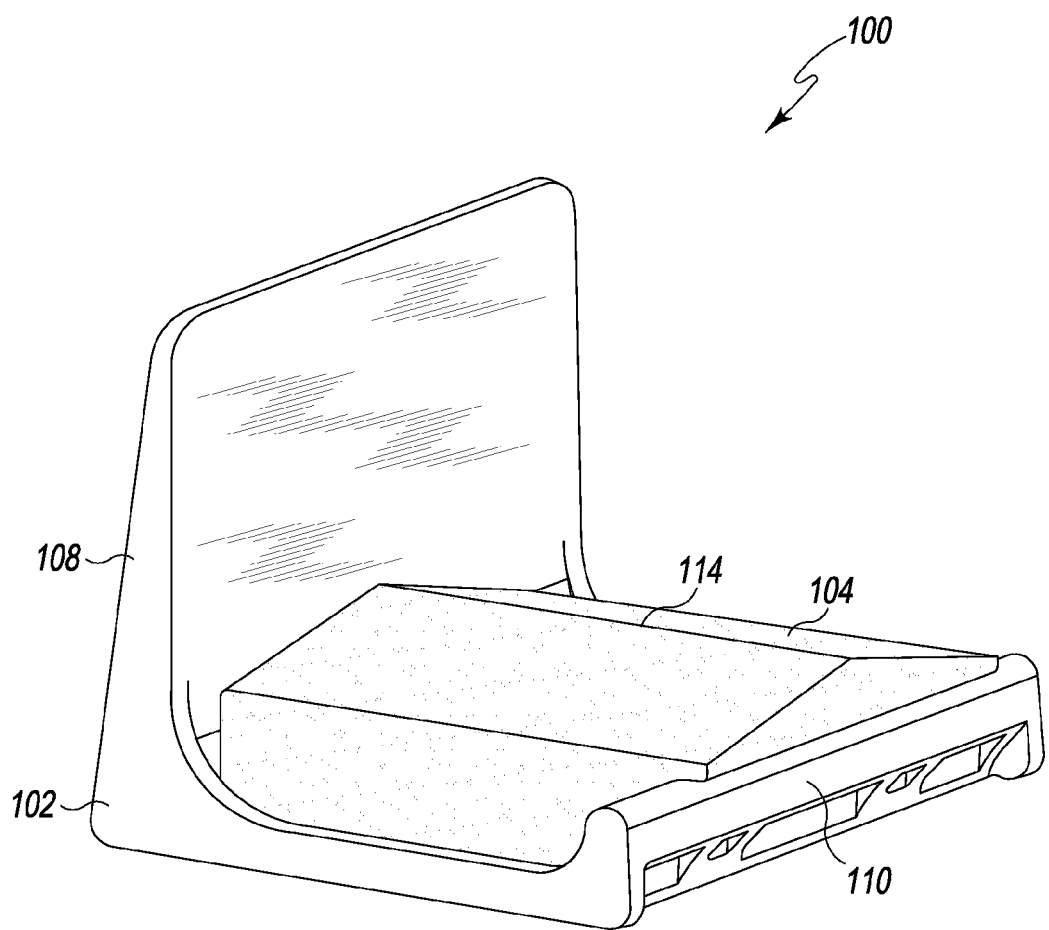
FIG. 10 is a perspective view of an x-ray calibration apparatus.
Figure 11:
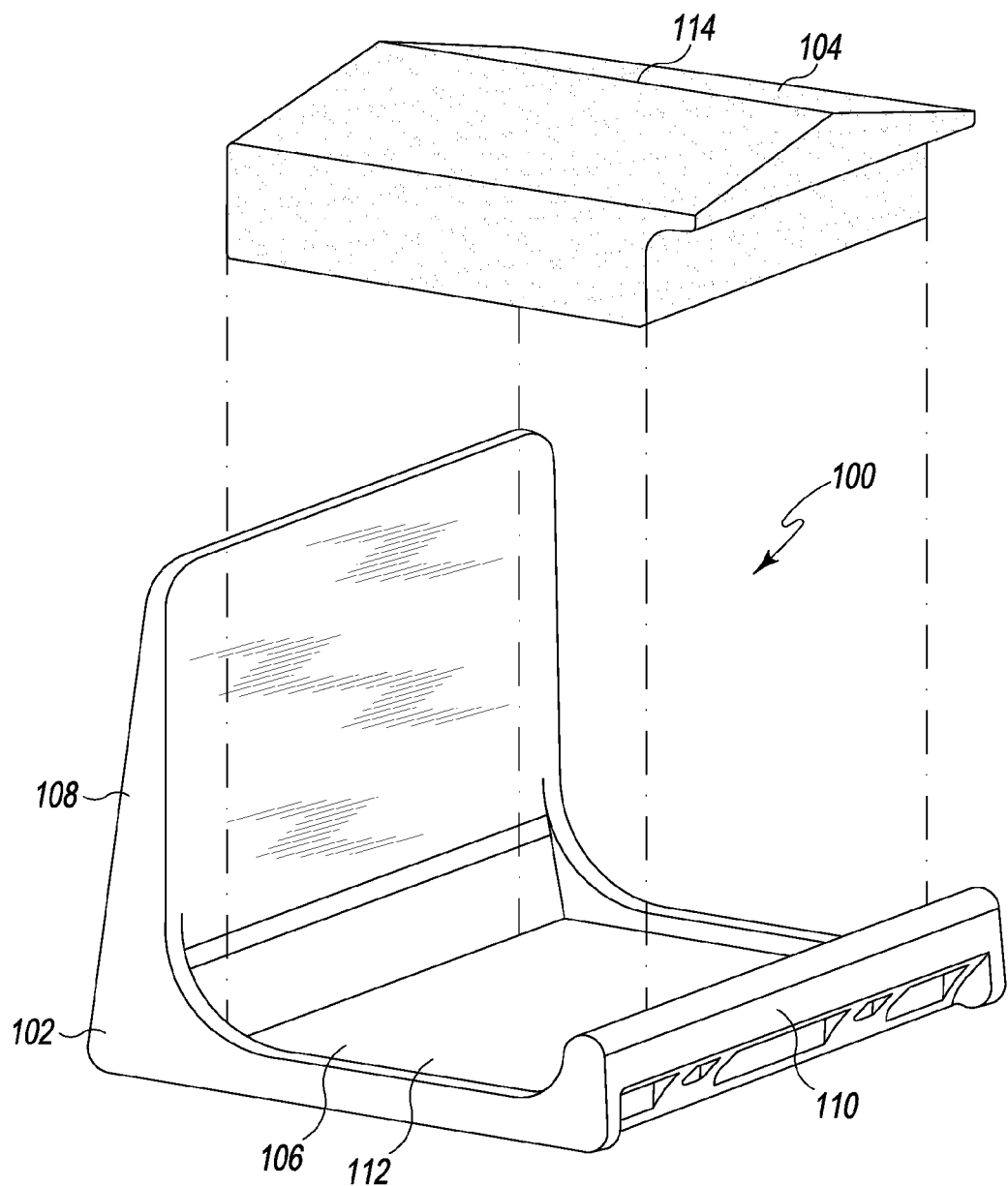
FIG. 11 is a perspective view of the x-ray calibration apparatus of FIG. 10, showing the radiolucent cushion removed.

Referring now to FIGS. 10-11, an x-ray calibration apparatus 100 is illustrated. As will be described below in greater detail, the x-ray calibration apparatus 100 enables x-ray imaging and accurate three-dimensional reconstruction of a patient's bony anatomy. The x-ray calibration apparatus 100 includes a radiolucent knee alignment jig 102 and a radiolucent cushion 104. The radiolucent knee alignment jig 102 is formed from a radiolucent plastic and is configured to receive a patient's knee 130. The knee alignment jig 102 includes a bottom plate 106, a lateral sidewall 108, and a medial sidewall 110. The lateral sidewall 108 and the medial sidewall 110 are secured to and extend upwardly from the bottom plate 106. In the illustrative embodiment described herein, the medial sidewall 110 is shorter than the lateral sidewall 108. The lateral sidewall 108 may be marked with intersecting perpendicular lines configured to be aligned with cross-hairs emitted by an x-ray source positioned to create an x-ray image taken perpendicularly to the sidewall. The bottom plate 106 includes a bottom surface 111 and an upper surface 112 configured to hold the radiolucent cushion 104. It should be appreciated that the x-ray calibration apparatus is intended to be suitable for use with patients having knees and bony anatomy of many different sizes. The bottom plate 106 is thus sufficiently wide to comfortably fit the knee of nearly any patient between the lateral sidewall 108 and the medial sidewall 110.

Figure 17:
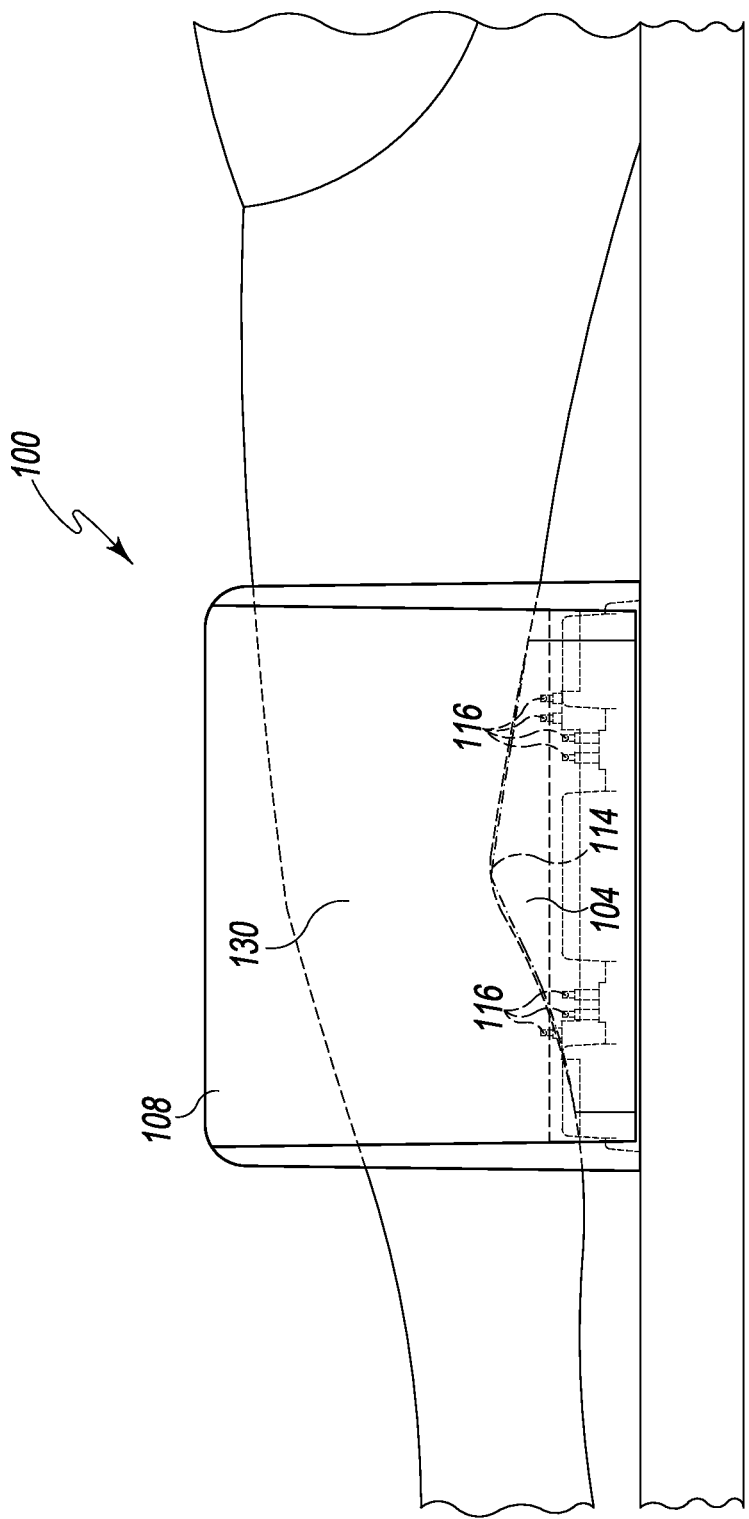
FIG. 17 is a side elevation view of a patient's knee positioned in the x-ray calibration apparatus of FIG. 10.

The radiolucent cushion 104 is secured to the upper surface 112 of the bottom plate 106 and positioned between the lateral sidewall 108 and the medial sidewall 110 of the radiolucent knee alignment jig 102. The radiolucent cushion 104 contains an upper ridge 114 and is angled to hold a patient's knee 130 at a fixed angle of flexion. In an embodiment, a knee flexion of approximately 5-10 may be used for x-ray imaging of the knee. The radiolucent cushion 104 is also configured to hold the patient's knee 130 at a fixed distance above the x-ray table, as shown in FIG. 17. The radiolucent cushion 104 is made of a soft material so as to be comfortable to the patient. The radiolucent cushion 104 may be marked with instructions useful to the x-ray technician or other healthcare provider in the placement of the x-ray calibration apparatus 100 and in placement of a patient's knee 130. The radiolucent cushion 104 may also be marked with intersecting perpendicular lines configured to be aligned with cross-hairs emitted by an x-ray source positioned to create an x-ray image taken perpendicularly to the bottom plate 106.

Figure 12:
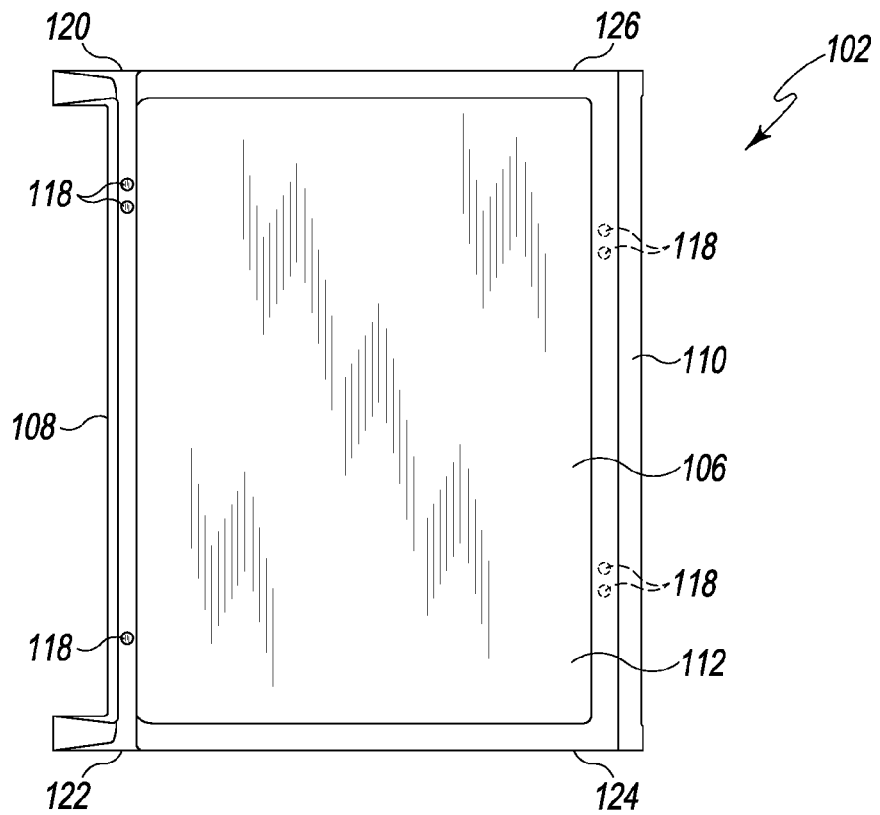
FIG. 12 is an anterior elevation view of the x-ray calibration apparatus of FIG. 10 with the radiolucent cushion removed.
Figure 13:
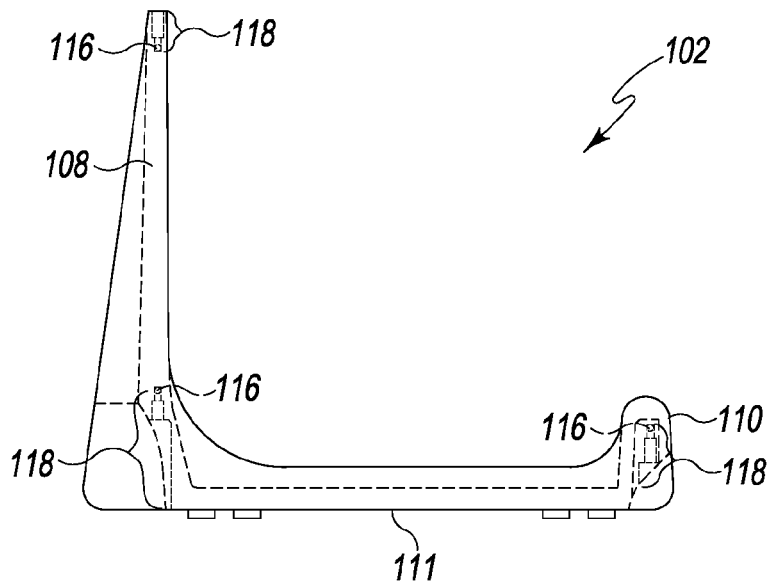
FIG. 13 is an elevation view of the x-ray calibration apparatus of FIG. 10 with the radiolucent cushion removed.
Figure 20:
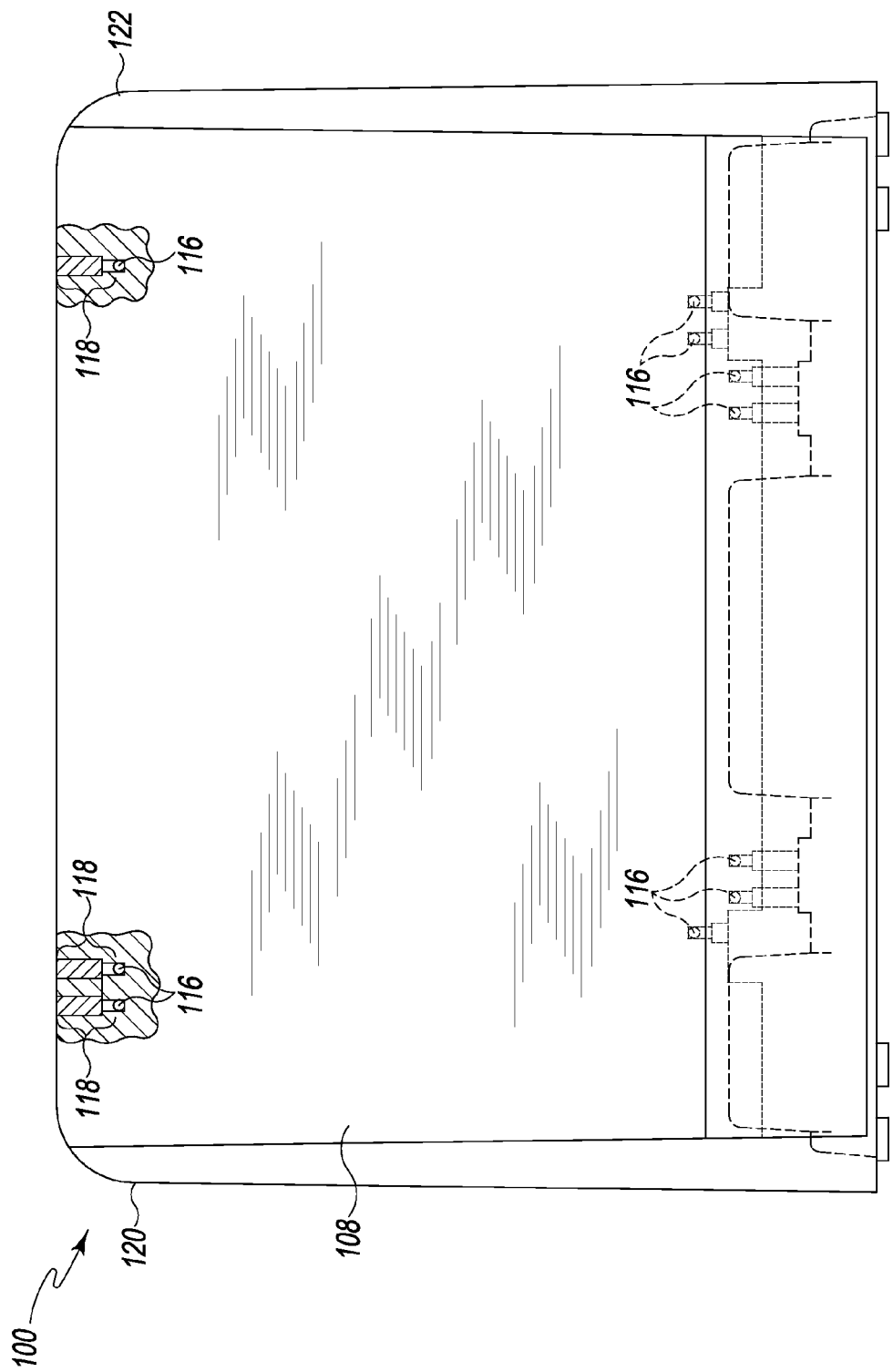
FIG. 20 is a side elevation view of the x-ray calibration apparatus of FIG. 10.

As depicted in FIGS. 12-13, as well as in FIGS. 17 and 20, within the radiolucent lateral sidewall 108 and the radiolucent medial sidewall 110 there are located a plurality of fiducial markers 116. The fiducial markers 116 are radio-opaque such that when viewed on x-ray images of a patient's knee 130 in the x-ray calibration apparatus 100, the representations 138 of the fiducial markers 116 provide registration points that can be used to calculate the x-ray scaling factor and beam angle and to register multiple x-ray images onto one another. The fiducial markers 116 may be made of any radio-opaque material. In the illustrative embodiment described herein, the fiducial markers 116 are embodied as metal ball bearings.

In the illustrative embodiment described herein, the lateral sidewall 108 and medial sidewall 110 have a number of blind bores 118 formed therein. Embedded within each of the blind bores 118 is one of the fiducial markers 116. The remainder of each of the blind bores 118 is filled with a radiolucent material such as a plastic plug or the like. In other embodiments, the fiducial markers 116 may be embedded in the lateral sidewall 108 and the medial sidewall 110 by other means. It should be understood that however the fiducial markers 116 are embedded, they are held rigidly in position within the lateral sidewall 108 and the medial sidewall 110.

In the illustrative embodiment described herein, there are ten fiducial markers 116. As illustrated in FIGS. 12 and 20, three fiducial markers 116 are embedded near the top of the lateral sidewall 108. Of these three markers, two are located towards the distal edge 120 of the lateral sidewall 108 and the other is located towards the proximal edge 122 of the lateral sidewall 108.

As illustrated in FIGS. 17 and 20, three fiducial markers 116 are embedded near the bottom of the lateral sidewall 108. Of these three markers, two are located towards the proximal edge 122 of the lateral sidewall 108 and the other is located towards the distal edge 120 of the lateral sidewall 108.

As illustrated in FIGS. 12, 17, and 20, the remaining four fiducial markers 116 are embedded within the medial sidewall 110. Of these four markers, two are located towards the proximal edge 124 of the medial sidewall 110 and the other two are located towards the distal edge 126 of the medial sidewall 110.

While the positions of the fiducial markers 116 in the illustrative embodiment described herein have been described in detail, other arrangements may be used given the needs of different modeling systems, given the need for more or fewer registration points on x-ray images, or given the need for registration points in different locations on x-ray images. However, it should be understood that, when viewed on x-ray images taken in a direction anterior to the patient's knee 130 or in a direction lateral to the patient's knee 130, none of the fiducial markers 116 overlaps with any other fiducial marker or with the bony anatomy of the patient. Further, in such an embodiment some fiducial markers 116 are in front of the bony anatomy and others are behind the bony anatomy in both anterior and lateral views.

It should be appreciated that the x-ray calibration apparatus 100 is suitable for use with patients having knees and bony anatomy of many different sizes. Thus, fiducial markers 116 embedded near the top of the lateral sidewall are positioned high enough to appear above the bony anatomy of a given patient's knee when the marker's representations are viewed on a lateral x-ray image. Similarly, the fiducial markers 116 embedded within the medial sidewall 110 and those embedded near the bottom of the lateral sidewall 108 are positioned low enough to appear below the bony anatomy of a given patient's knee when the marker's representations are viewed on a lateral x-ray image.

As described above, the radiolucent cushion 104 functions to hold the patient's knee 130 at a fixed distance above the x-ray table. As such, the radiolucent cushion is configured to hold the patient's knee 130 high enough off the table so that representations 138 of the fiducial markers 116 embedded within the medial sidewall 110 and of those embedded near the bottom of the lateral sidewall 108 appear below the patient's knee 130 when viewed on a lateral x-ray image 140 such as that shown in FIG. 19.

Figure 14:
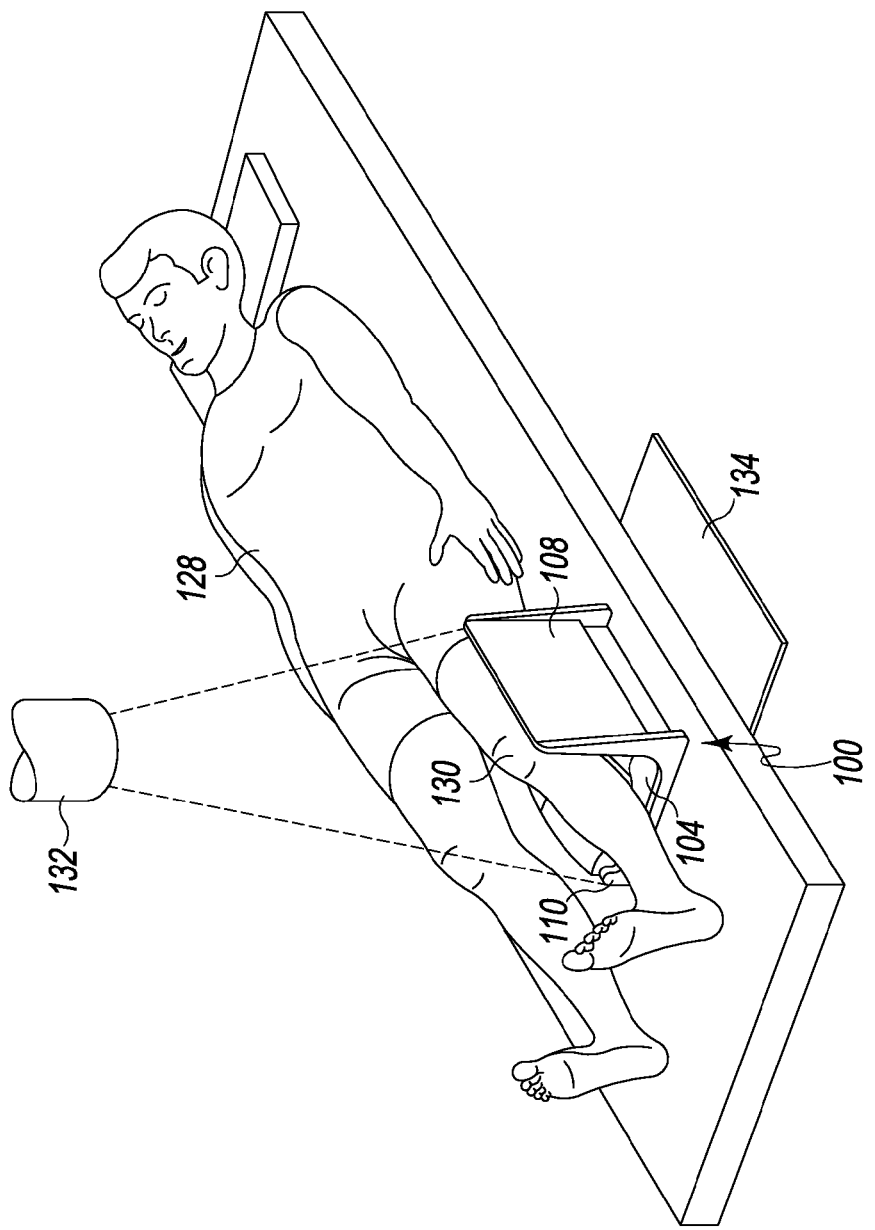
FIGS. 14-15 are perspective views of the x-ray calibration apparatus of FIG. 10 being used to position a patient's knee for an anterior x-ray and for a lateral x-ray, respectively.
Figure 15:
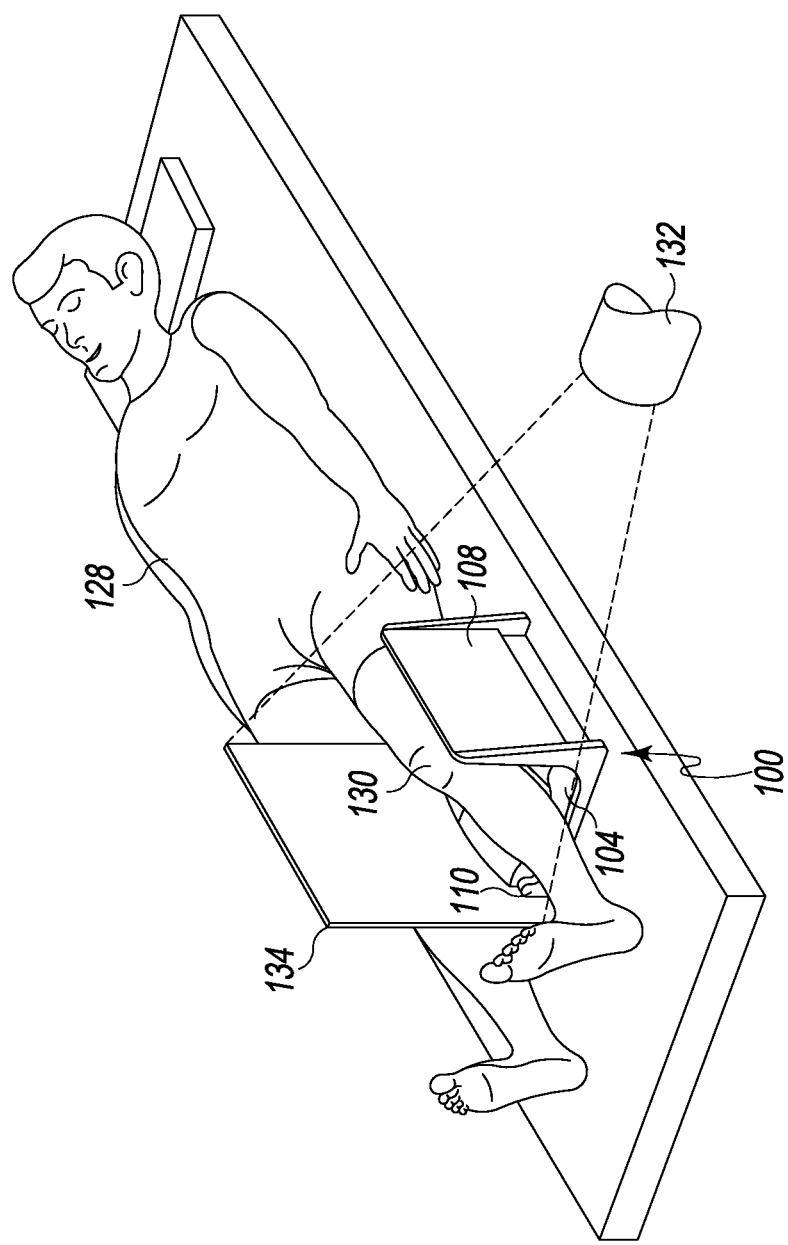
Figure 16:
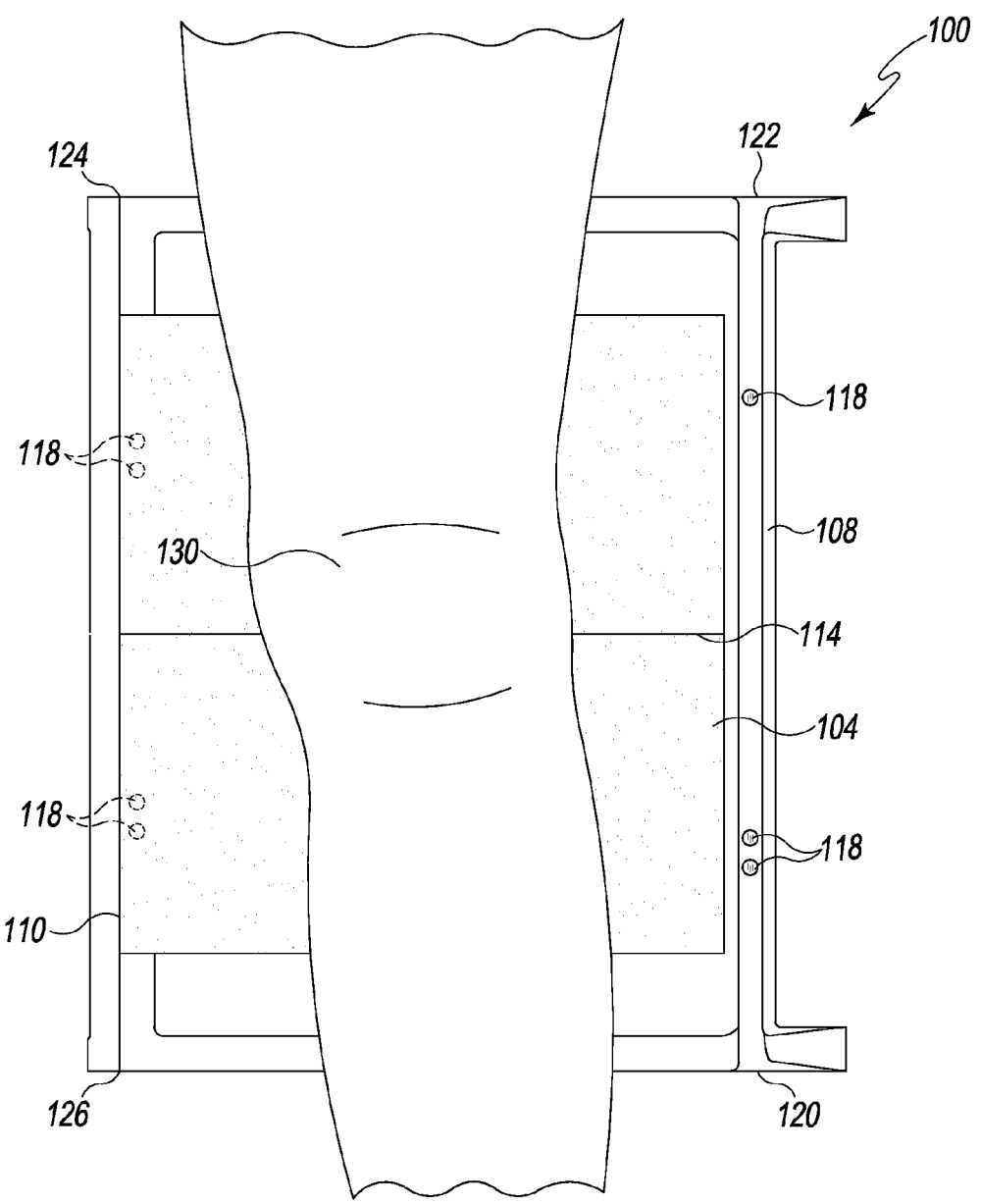
FIG. 16 is an anterior elevation view of a patient's knee positioned in the x-ray calibration apparatus of FIG. 10.

As shown in FIGS. 14-17, a patient 128 may be positioned with the patient's knee 130 in the x-ray calibration apparatus 100. As illustrated, the x-ray calibration apparatus 100 is positioned such that the lateral sidewall 108 is positioned outside the lateral side of the patient's knee 130, and the medial sidewall 110 is positioned outside the medial side of the patient's knee 130. As shown in FIGS. 14 and 16, an x-ray machine 132 and an x-ray cassette 134 may be positioned to acquire an x-ray image taken in a direction anterior to the patient's knee 130. As can be seen in FIGS. 15 and 17, the x-ray machine 132 and the x-ray cassette 134 may also be positioned to acquire an x-ray image taken in a direction lateral to the patient's knee.

Figure 18:
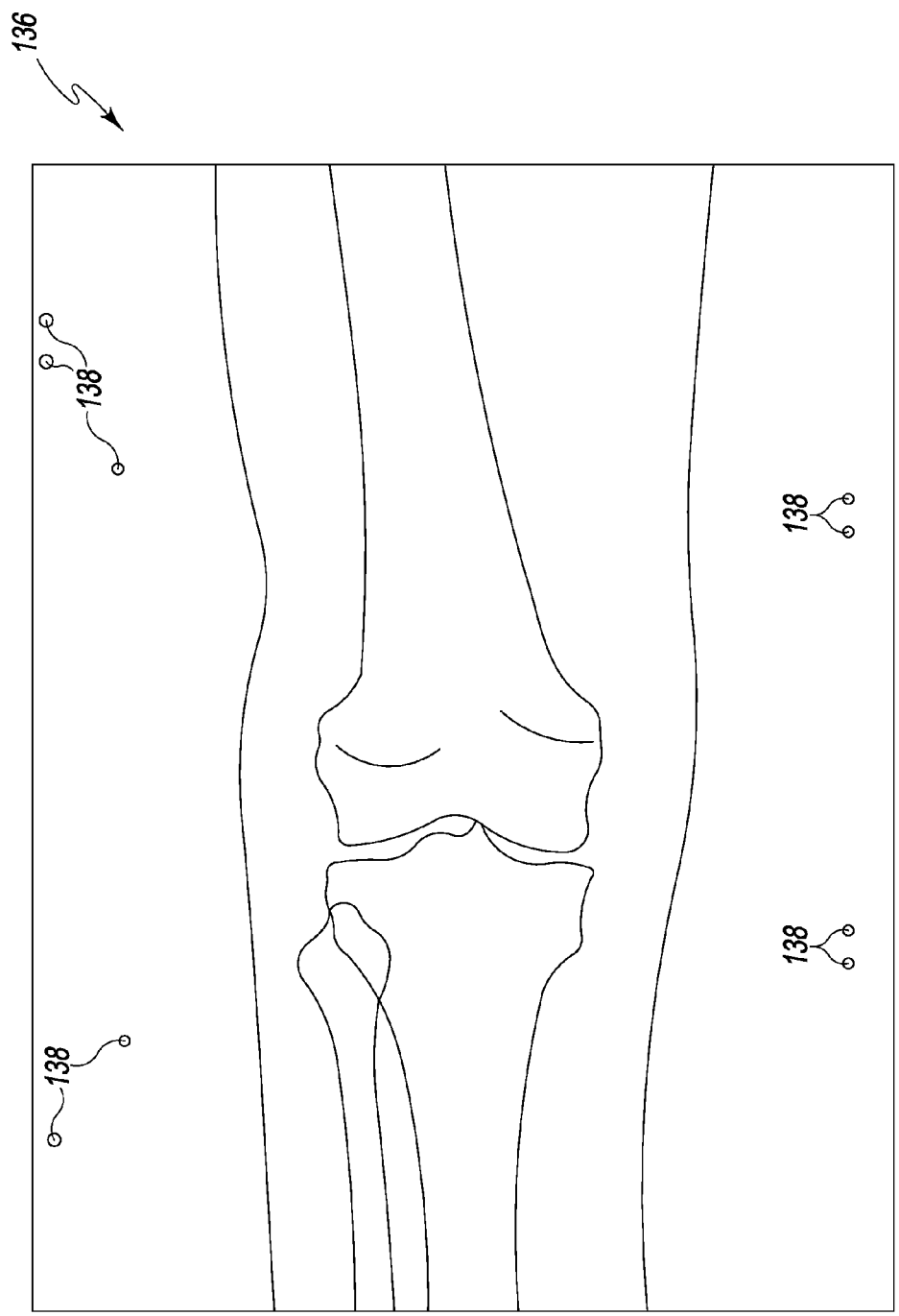
FIG. 18 is an anterior x-ray image of a patient's knee taken using the x-ray calibration apparatus of FIG. 10.

Referring now to FIG. 18, an anterior x-ray image 136 is taken in a direction anterior to a patient's knee 130. The anterior x-ray image 136 includes representations 138 of the fiducial markers 116. There are four representations 138 medial to the bony anatomy of the patient's knee 130, with such representations 138 corresponding to the four fiducial markers 116 located in the medial sidewall 110 of the illustrative embodiment described herein. As can also be seen in FIG. 18, six representations 138 are located laterally to the bony anatomy of the patient's knee 130, with such representations 138 corresponding to the six fiducial markers 116 located in the lateral sidewall 108 of the illustrative embodiment described herein. As can be seen, none of the representations 138 of the fiducial markers 116 overlaps with any of the other representations 138 or with the bony anatomy of the patient's knee 130 when viewed on an anterior x-ray image 136.

Figure 19:
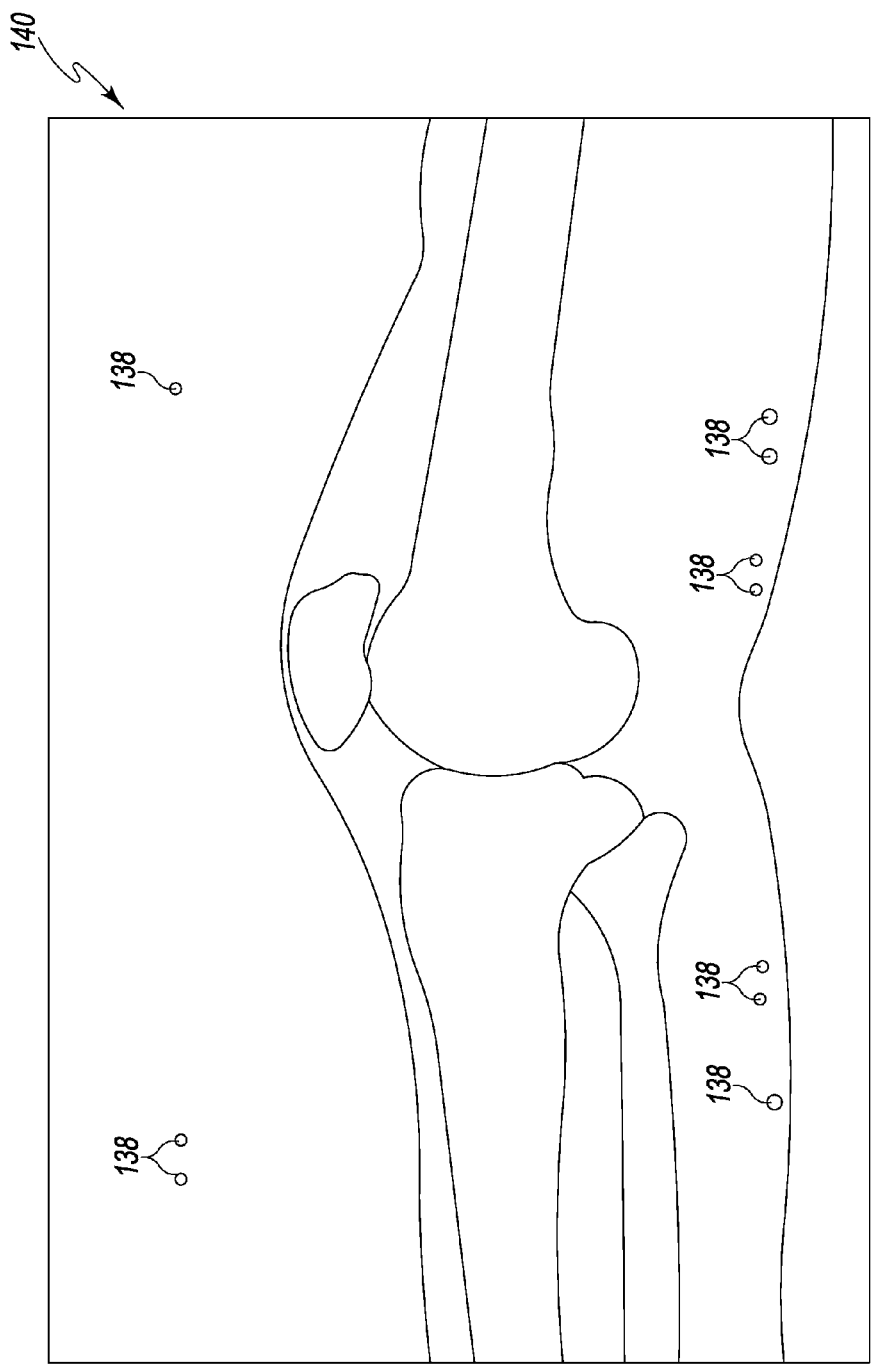
FIG. 19 is a lateral x-ray image of a patient's knee taken using the x-ray calibration apparatus of FIG. 10.

A lateral x-ray image 140 taken in a direction lateral to the patient's knee 130 is shown in FIG. 19. Like the anterior x-ray of FIG. 18, the lateral x-ray image 140 also includes representations 138 of the fiducial markers 116. For example, three representations 138 are shown located above the bony anatomy of the patient's knee 130, with such representations 138 corresponding to the three fiducial markers 116 located near the top of the lateral sidewall 108 of the illustrative embodiment described herein. As can also be seen in FIG. 19, seven representations 138 are located below the bony anatomy of the patient's knee 130. These seven representations 138 correspond to the four fiducial markers 116 located in the medial sidewall 110 and the three fiducial markers 116 located near the bottom of the lateral sidewall 108 of the illustrative embodiment described herein.

Using x-ray images of a patient's knee, such as those depicted in FIGS. 18 and 19, the x-ray scaling factor and beam angle can be calculated, and a three-dimensional image can be generated for use in the fabrication of a customized patient-specific orthopaedic knee instrument. The patient's knee is first positioned within the x-ray calibration apparatus 100 and properly aligned according to instructions provided therewith. As depicted in FIG. 14, an x-ray image is taken in a direction anterior to the patient's knee, resulting in an anterior x-ray image such as that shown in FIG. 18. As depicted in FIG. 15, an x-ray image is also taken in a direction lateral to the patient's knee, resulting in a lateral x-ray image such as that shown in FIG. 19. Using the representations 138 of the fiducial markers 116 as common registration points, the two x-ray images are then registered onto one another.

To calculate the x-ray scaling factor, the distances between two or more selected representations 138 of the fiducial markers 116 in either or both x-ray images are measured. These distances are then compared to the distances between the corresponding fiducial markers 116 in the x-ray calibration apparatus 100. The ratio of the distance between representations 138 over the distance between the corresponding fiducial markers 116 is equal to the x-ray scaling factor.

To calculate beam angle, the distances between two or more sets of representations 138 of the fiducial markers 116 in either or both x-ray images are measured. These distances are then compared to the distances between the corresponding fiducial markers 116 positioned in the x-ray calibration apparatus 100.

By registering the anterior and lateral x-ray images onto one another, a three-dimensional reconstruction of the patient's bony anatomy can be created. As described above in regard to FIGS. 1-9, such three-dimensional reconstruction of bony anatomy is used in creating patient-specific instruments. For example, one embodiment of the use of such three-dimensional images is described above in regard to process step 12.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. In particular, it is contemplated that the x-ray calibration apparatus, described above for use in generating x-ray images of a patient's knee, may also be used to generate x-ray images of other parts of a patient's anatomy.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

What is claimed is:

1. An x-ray calibration apparatus, comprising:
a radiolucent knee alignment jig configured to receive a knee of a patient, the knee alignment jig comprising (i) a bottom plate, (ii) a lateral sidewall secured to and extending upwardly from a lateral side of the bottom plate, and (iii) a medial sidewall secured to and extending upwardly from a medial side of the bottom plate,
a radiolucent cushion configured to hold a patient's knee at a fixed angle of flexion, the cushion being secured to an upper surface of the bottom plate and positioned between the lateral sidewall and the medial sidewall of the radiolucent knee alignment jig,
a first plurality of radio-opaque fiducial markers positioned within the lateral sidewall, comprising (i) an upper lateral plurality of radio-opaque fiducial markers, positioned within the lateral sidewall such that when viewed in an x-ray image taken perpendicularly to the lateral sidewall, each of the upper lateral plurality of radio-opaque fiducial markers appears above an upper ridge of the radiolucent cushion, and (ii) a lower lateral plurality of radio-opaque fiducial markers, positioned within the lateral sidewall such that when viewed in an x-ray image taken perpendicularly to the lateral sidewall, each of the lower lateral plurality of radio-opaque fiducial markers appears below the upper ridge of the radiolucent cushion, and
a second plurality of radio-opaque fiducial markers positioned within the medial sidewall, wherein the second plurality of radio-opaque fiducial markers are positioned such that (i) when viewed in an x-ray image taken perpendicularly to the bottom plate, each of the second plurality of radio-opaque fiducial markers are distinct from the first plurality of radio-opaque fiducial markers, and (ii) when viewed in an x-ray image taken perpendicularly to the lateral sidewall, each of the second plurality of radio-opaque fiducial markers are distinct from the first plurality of radio-opaque fiducial markers.

2. The x-ray calibration apparatus of claim 1, wherein:
the medial sidewall is shorter than the lateral sidewall.

3. The x-ray calibration apparatus of claim 1, wherein:
the upper lateral plurality of radio-opaque fiducial markers consists of three radio-opaque fiducial markers,
the lower lateral plurality of radio-opaque fiducial markers consists of three radio-opaque fiducial markers, and
the second plurality of radio-opaque fiducial markers consists of four radio-opaque fiducial markers.

4. An x-ray calibration apparatus, comprising:
a radiolucent knee alignment jig configured to receive a knee of a patient, the knee alignment jig comprising (i) a bottom plate, (ii) a lateral sidewall secured to and extending upwardly from a lateral side of the bottom plate, and (iii) a medial sidewall secured to and extending upwardly from a medial side of the bottom plate, the medial sidewall being parallel to, and shorter than, the lateral sidewall,
a radiolucent cushion configured to hold a patient's knee at a fixed angle of flexion, the cushion being secured to an upper surface of the bottom plate and positioned between the lateral sidewall and the medial sidewall,
a first plurality of radio-opaque fiducial markers, positioned such that when viewed in an x-ray image taken perpendicularly to the lateral sidewall, each of the first plurality of radio-opaque fiducial markers appears above an upper ridge of the radiolucent cushion,
a second plurality of radio-opaque fiducial markers, positioned such that when viewed in an x-ray image taken perpendicularly to the lateral sidewall, each of the second plurality of radio-opaque fiducial markers appears below the upper ridge of the radiolucent cushion, and
a third plurality of radio-opaque fiducial markers positioned such that (i) when viewed in an x-ray image taken perpendicularly to the bottom plate, each of the third plurality of radio-opaque fiducial markers is distinct from each of the first and second plurality of radio-opaque fiducial markers, and (ii) when viewed in an x-ray image taken perpendicularly to the lateral sidewall, each of the third plurality of radio-opaque fiducial markers is distinct from each of the first and second plurality of radio-opaque fiducial markers.

5. The x-ray calibration apparatus of claim 4, wherein:
the radiolucent cushion is marked with intersecting perpendicular lines configured to be aligned with cross-hairs emitted by an x-ray source positioned to create an x-ray image taken perpendicularly to the bottom plate, and
the lateral sidewall is marked with intersecting perpendicular lines configured to be aligned with cross-hairs emitted by an x-ray source positioned to create an x-ray image taken perpendicularly to the lateral sidewall.

6. The x-ray calibration apparatus of claim 4, wherein:
the first plurality of radio-opaque fiducial markers are positioned within the lateral sidewall, the second plurality of radio-opaque fiducial markers are positioned within the lateral sidewall, and the third plurality of radio-opaque fiducial markers are positioned within the medial sidewall.

7. The x-ray calibration apparatus of claim 4, wherein:

the first plurality of radio-opaque fiducial markers consists of three radio-opaque fiducial markers, the second plurality of radio-opaque fiducial markers consists of three radio-opaque fiducial markers, and the third plurality of radio-opaque fiducial markers consists of four radio-opaque fiducial markers.

\* \* \* \* \*